US008320517B2

(12) United States Patent
Dennerlein

(10) Patent No.: US 8,320,517 B2
(45) Date of Patent: Nov. 27, 2012

(54) X-RAY SYSTEM AND METHOD FOR THE GENERATION OF A SCAN PATH

(75) Inventor: Frank Dennerlein, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 150 days.

(21) Appl. No.: 12/902,236

(22) Filed: Oct. 12, 2010

(65) Prior Publication Data
US 2011/0085636 A1 Apr. 14, 2011

(30) Foreign Application Priority Data
Oct. 12, 2009 (DE) .......................... 10 2009 049 075

(51) Int. Cl.
*A61B 6/03* (2006.01)
(52) U.S. Cl. .......................................................... 378/4
(58) Field of Classification Search ................ 378/4, 19, 378/21
See application file for complete search history.

(56) References Cited

U.S. PATENT DOCUMENTS
4,200,799 A 4/1980 Saito
2006/0126779 A1* 6/2006 Basu et al. ........................ 378/4

FOREIGN PATENT DOCUMENTS
DE 102006037564 B3 3/2008

OTHER PUBLICATIONS
Kyriakou et al, "Simultaneous misalignment correction for approximate circular cone-beam computed tomography", 2008 Phys. Med. Biol. 53, pp. 6267-6289; Magazine; 2008.

* cited by examiner

*Primary Examiner* — Irakli Kiknadze

(57) ABSTRACT

A method for generation of a scan path for an x-ray source and/or an x-ray detector of an x-ray system is provided. CT-type imaging on the x-ray system is enabled by traversing the scan path upon simultaneous acquisition of a series of x-ray images. An original scan path of the x-ray source and/or of the x-ray detector is provided, where the scan path is defined by a series of original acquisition points. A viewing axis from the x-ray source to the object and/or the detector is identified for at least one acquisition point on the scan path. A modified scan path is generated by displacement of the at least one acquisition point at least partially along the viewing axis so that the scanning movement upon traversing the modified scan path can be reproduced as in the original scan path.

12 Claims, 4 Drawing Sheets

II

III

X-RAY SYSTEM AND METHOD FOR THE GENERATION OF A SCAN PATH

CROSS REFERENCE TO RELATED APPLICATIONS

This application claims priority of German application No. 10 2009 049 075.2 filed Oct. 12, 2009, which is incorporated by reference herein in its entirety.

FIELD OF THE INVENTION

The invention relates to an x-ray system and a method for CT-type imaging. The x-ray system has an x-ray source and an x-ray detector, which can be moved along a scan path which is as a rule preprogrammed. CT-type imaging is enabled by means of traversing of the scan path upon simultaneous acquisition of a series of x-ray images. The method is used to generate a scan path for an x-ray source and an x-ray detector of the x-ray system.

BACKGROUND OF THE INVENTION

Computer tomography (CT) is a method of medical imaging. Here the spatial density distribution of an object, as a rule of a patient, is reconstructed from a series of two-dimensional projection images. The projection images are thereby acquired from different angles of view with a scanner apparatus comprising x-ray source and x-ray-sensitive detector. In order to reconstruct object density distribution with a high level of quality, it is necessary to know the precise position and orientation of x-ray source and detector.

In computer tomography both tube-like systems (computer tomographs) and also C-arm devices are known. Here the x-ray source is moved in a circular scan path around the object to be represented, while the detector is arranged in opposition to it. The reconstruction of the image data takes place on the basis of algorithms, which are adjusted according to the exact scan path of the x-ray source and the detector.

In order to guarantee or improve access to the patient during the x-ray procedure, scanner systems are called for whose x-ray source and detector are mounted on individually actuatable moving arms. These are for example moved in a motorized manner with the aid of rails and joints and thus have a high degree of freedom in their movement. General mechanical inaccuracies arise hereby, which lead to imprecise geometric data. Imprecise geometric data in turn results in image artifacts in the reconstruction result. If the mechanical inaccuracies mount up as a result of a multiplicity of actuation steps of the movement, this can result in the object to be represented no longer being capable of reconstruction.

SUMMARY OF THE INVENTION

The object underlying the invention is to enable imaging on an x-ray system with individually movable x-ray source or x-ray detector, whose image quality is improved, whereby image artifacts are reduced.

To solve this problem the invention proposes a method, an x-ray system and a computer program product according to the claims.

The inventive method is used to generate a scan path for an x-ray source and/or an x-ray detector of an x-ray system. By traversing the scan path upon the simultaneous acquisition of a series of x-ray images, CT-type imaging on the x-ray system is enabled. This takes place with the following steps:

Provision of an original scan path of the x-ray source and/or of the x-ray detector, where the scan path is defined by means of a series of original acquisition points;

for at least one original acquisition point on the scan path, identification of a viewing axis from the x-ray source to the object and/or the detector;

generation of a modified scan path by means of displacement of at least one acquisition point, at least partially along the viewing axis, so that the scanning movement during traversing of the modified scan path can be reproduced as in the case of the original scan path.

The original scan path is based on original acquisition points, which are preferably arranged at regular distances, and whose geometric data (spatial position) is known. A high number of acquisition points (for example 150 to 400, preferably 200 to 300) enables high-quality imaging. The viewing axis is the axis that runs from the x-ray source to the object or from the x-ray source through the object to the detector. The viewing axis defines the direction of view, with which the respective projection image or x-ray image is acquired. By means of the displacement of one or more acquisition points along the associated viewing axis, the geometric data of a modified scan path can also be recorded. According to the invention a modified scan path can be traversed, which can be reproduced like the original scan path. This has the advantage that the actuation of the x-ray source and/or of the x-ray system need not be adjusted to the originally prescribed scan path. Upon traversing the scan path the x-ray system thus performs movements that may be better reproduced and thus permit a higher degree of mechanical reproduction capability. As the viewing angle of the individual x-ray images is not changed by a displacement along the viewing axis, the innovative method exhibits no additional problems in implementation. The data record made with the modified scan path essentially contains the same information as a data record which can be achieved with the aid of the original scan path. In the case of the modified scan path too, high quality reconstruction of the image data is thus guaranteed.

The x-ray source and/or the x-ray detector can advantageously be moved on a carrier device with different degrees of freedom. Such a carrier device can thus be moved in both a translatory and/or rotational manner, with it being possible for instance for these to be used in the form of telescopic arms, rail mechanisms/rail hangers or also robot arms.

Particularly preferably the x-ray system requires fewer motors and/or motor movements for traversing the modified scan path than for traversing the original scan path. By means of a smaller number of motors for controlling the translations and rotations of the x-ray system the reproduction accuracy of the system movement is increased. This depends on the fact that a more precise traversing is enabled, as the mechanical inaccuracies occurring with every motor movement are reduced by means of the smaller number of motors or motor movements respectively.

The viewing axis for example runs through the focal spot of the x-ray source and a defined point on the detector, for example its center. The location of the viewing axis for each acquisition point is precisely defined.

The motor movements necessary for traversing the original scan path and the modified scan path are preferably programmed in the x-ray system. The accuracy of reproduction is thereby optimized. The system reliably has recourse to the geometric data of the original scan path and the modified scan path. The motor movements and the geometric data for acquisition of x-ray images are harmonized with each other.

According to a first embodiment the modified scan path is calculated from the original scan path by means of an analytical method. The algorithm can for example investigate the original scan path—with all the programmed motor movements—for such motors/degrees of freedom that are actuated only over minor stretches, and shut down these motors completely. Alternatively based on knowledge of the arrangement of the carrier device and their dynamics with all the present telescopic arms, rails and swivel joints, a scan path can be analytically calculated which has a similar course to the original scan path, for example only diverges from it by a particular distance (measured radially and/or in the circumferential direction), or has the same start and end point.

According to another embodiment the modified scan path is calculated by means of a numeric method, for example an iterative method. This can for example happen by means of a mathematical cost function being defined which describes the entire motor activity during the traversing of the trajectory. This cost function could for example rely on the analysis of the difference in the motor attitudes of respective adjacent distance points. In addition the movement of each individual motor could affect the cost function to a different extent, depending on how precisely the particular motor can be controlled. The original scan path is then modified according to the defined degrees of freedom and with an iterative method in such a way that the cost function (and thereby the motor activity) is reduced. The result of this process is a scan path that requires fewer motor movements, and thus exhibits greater mechanical stability.

The original scan path is preferably made up of one or a number of straight lines. The geometric data of the original scan path is thus known and readily calculable. A scan path made up of straight lines is for example selected, because it could be assumed that these are traversable in a particularly reproducible manner on an x-ray system to which source and detector are attached on telescopic arms, rails or the like. However as the scan path does not describe the movement of the telescopic aim, but the movement of the focal spot of the x-ray source or the movement of the detector, which under certain circumstances are articulated on the telescopic aim by means of further intermediate pieces, this original assumption is not always correct. Accordingly a scan path which is composed of straight lines can also necessitate a complex interaction of motor movements during the traversing. The original scan path preferably forms at least a section of a rectangular path.

The modified scan path follows for example an at least partially curved course. This can depend on the fact that the complicated interaction of motor movements is foregone, and the telescopic aim is now driven in a straight line. Because of the divergent movement of the intermediate pieces the actual path of the x-ray source or of the detector now no longer runs in a straight line, but in a curve. The modified scan path can in one embodiment follow at least partially the original scan path or in one or more sections follow the original scan path or in another embodiment diverge completely from the original scan path.

According to a preferable embodiment the carrier device of the x-ray source and/or of the x-ray detector at least partially traverses the original scan path in the modified scan path. The carrier device comprises for example a carrier arm movable in a translatory manner along a vertical axis and a horizontal axis. On its tip is located for example a rotationally arranged intermediate piece, which swivels the x-ray source or the x-ray detector into position. With a suitable number of the modified scan path the modified scan path corresponds to the movement of the x-ray source or x-ray detector upon traversing of the original scan path by the carrier device. Accordingly, the scan path can be traversed with fewer motors/motor movements. This offers the advantage that the actuation of the movement has a higher mechanical reproducibility, and at the same time high quality image reconstruction of the modified scan path is guaranteed.

The invention also relates to the x-ray system with an x-ray source and/or an x-ray detector, which in each case can be moved along a preprogrammed scan path, where by means of traversing of the scan path upon simultaneous acquisition of a series of x-ray images, a CT-type imaging is enabled. The x-ray system encompasses a computer system, which is designed to generate a scan path in which the method described above can be executed. The method can be embodied according to one of the claims 1 to 10.

In addition the invention relates to computer program product with computer-readable software code segments for the generation of a scan path for an x-ray source and/or an x-ray detector of an x-ray system, where by means of traversing of the scan path upon simultaneous acquisition of a series of x-ray images, a CT-type imaging on the x-ray system is possible. The computer program product is designed to cause a computer to perform the steps of the method described above, when the program runs on the computer.

The invention also relates to a computer program as such and to a computer-readable medium or digitally readable medium, on which such a computer program is stored.

BRIEF DESCRIPTION OF THE DRAWINGS

The invention is described below on the basis of preferred exemplary embodiments in FIGS. 1-7, where.

DETAILED DESCRIPTION OF THE INVENTION

Figure 1:
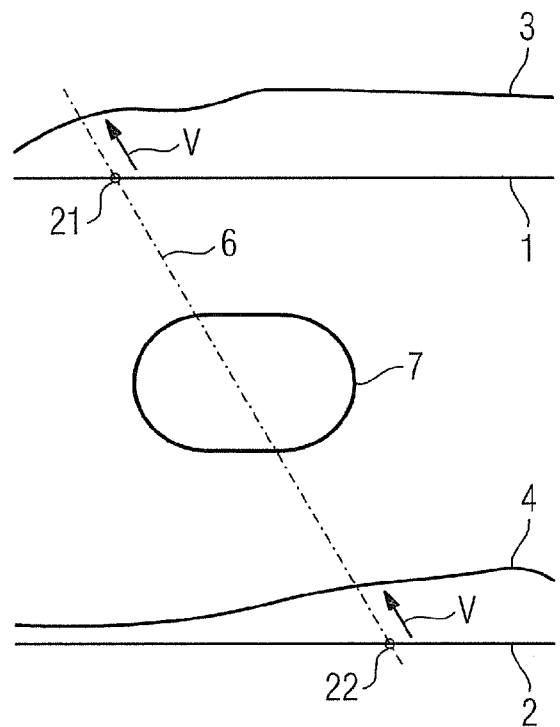
FIG. 1 shows in diagrammatic form the location of the viewing axis through the object to be represented and the scan paths.

FIG. 1 shows in diagrammatic form the location of the viewing axis 6 to a system attitude in the original scan path 1 of the x-ray source, from which a recording is provided for. The viewing axis 6 runs through the original scan path 1 of the x-ray source, where their point of intersection forms an acquisition point 21. The viewing axis 6 additionally runs through a central point of the object 7 to be imaged. In this exemplary embodiment the viewing axis 6 also intersects the original scan path 2 of the x-ray detector, where their point of intersection forms a second acquisition point 22.

The acquisition point 21 is distanced along the image axis by the displacement V from the original scan path 1 of the x-ray source. The location of the corresponding acquisition point 21 on a modified scan path 3 of the x-ray source is determined by the displacement V.

FIG. 1 only shows sections of the original and modified scan path, as only one system attitude is being examined here.

The acquisition point 22 of the original scan path 2 of the x-ray detector is distanced by the displacement V of the original scan path 2. The location of the acquisition points 22 on a modified scan path 4 of the x-ray detector is determined by the displacement V. In this exemplary embodiment the displacement V of the acquisition points 21, 22 takes place both for an x-ray source and for the detector. It is however also possible that the displacement V of acquisition points only takes place for the x-ray source or for the detector.

In each system attitude, the corresponding acquisition points are recorded which form the modified scan path based on a multiplicity of system attitudes.

Figure 2:
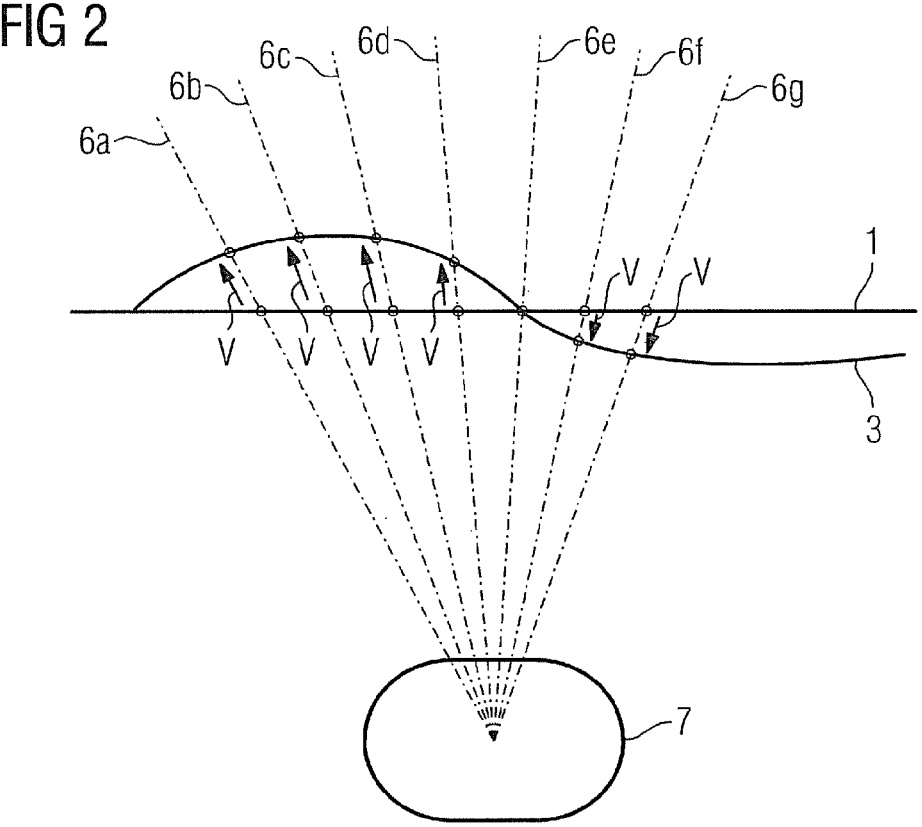
FIG. 2 shows in diagrammatic form an exemplary embodiment for generation of a modified scan path.

FIG. 2 illustrates the generation of a modified scan path 3 by means of a displacement V of acquisition points of the original scan path 1, here represented as points of intersection of the original scan path 1 with the respective viewing axis 6a-g. In this exemplary embodiment the viewing axis 6a-g runs at each acquisition point from the x-ray source to the object to be represented 7. The original scan path of the x-ray source 1 and the modified scan path of the x-ray source 3 are represented. The viewing axes 6a-g in each case correspond to a system attitude, where for each viewing axis 6a-g an acquisition point on the original scan path 1 is provided. The displacement V of the acquisition points can take place in different directions, preferably along the viewing axes 6a-6g, as shown in FIG. 2. It is also possible that for particular viewing axes (for example 6e) no displacement of the original acquisition point takes place. The displacement along the viewing axes makes it possible to retain the angle of view with the displacement V, although minimal divergences (for example up to approx. 20°) are permissible. The original scan path 1 of the x-ray source is here a straight line, while the modified scan path 3 of the x-ray source follows a curved course.

Figure 3:
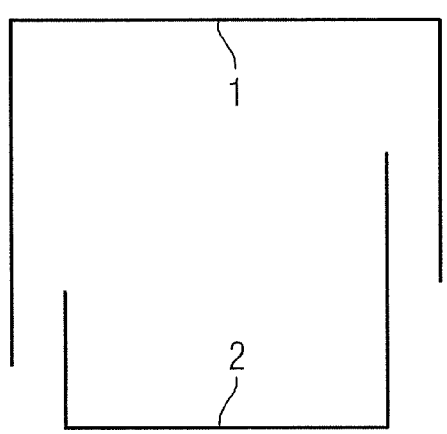
FIG. 3 shows in diagrammatic form an exemplary embodiment for original scan paths.
Figure 3:
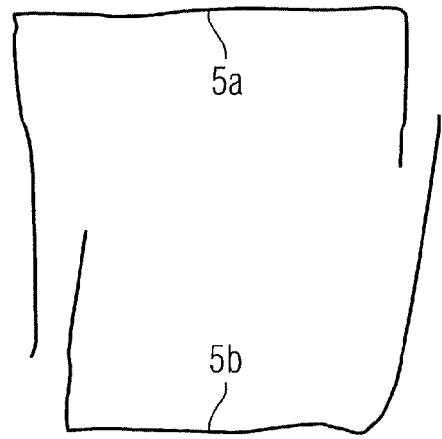
Figure 4:
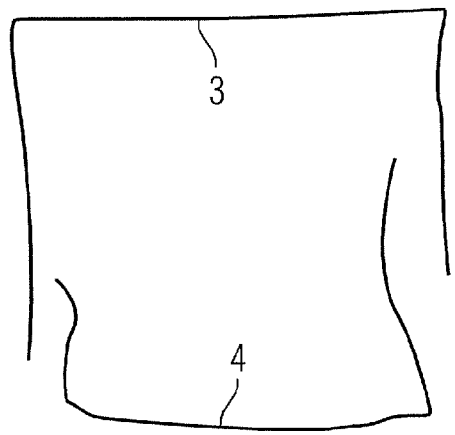
FIG. 4 shows in diagrammatic form an exemplary embodiment for modified scan paths.
Figure 4:
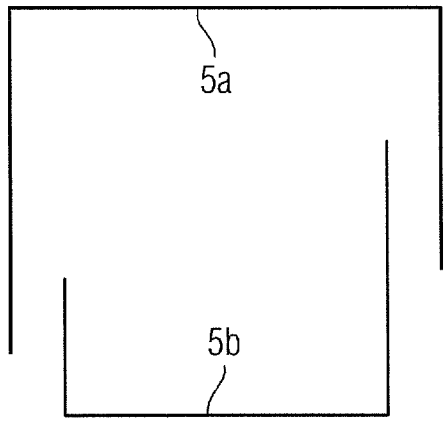

FIG. 3 and FIG. 4 show an exemplary embodiment. FIG. 3 shows in diagrammatic form the original scan paths of the x-ray source 1 and of the x-ray detector 2. The scan paths form a rectangular path. The actual movement of the carrier arm tip 5a, 5b of the carrier arm, to which the x-ray source 9 or the x-ray detector 10 is assigned does not run, like the original scan path, in a straight line. This depends on the fact that an intermediate piece 11 is in each case arranged on the carrier arm tip, via which the x-ray source 9 or the detector 10 is swiveled in the direction of view during the scanning movement. Accordingly, the carrier arm 8 must be adjusted to this swiveling movement of the intermediate piece in the horizontal, as well as in the vertical direction. This in turn requires many different motors or motor movements, which is however to be avoided. FIG. 4 shows the correspondingly modified scan paths of the x-ray source 3 and of the x-ray detector 4. These paths are no longer defined like the original scan paths 1, 2, but follow a curved course. These scan paths 3, 4 correspond to the actual scan paths of the x-ray source and of the x-ray detector itself. In the modified scan path the movements of the carrier arm tips 5a, 5b now take place in a straight line and broadly correspond to the original scan path 1, 2. This offers the advantage that the actuation of the carrier arms or the carrier device 8 can now take place in a simpler manner, that is to say with fewer motors or with fewer motor movements; this is because a complex adjustment of the position of the x-ray source 9 or of the detector 10 to a prescribed (original) scan path is here dispensed with.

Figure 5:
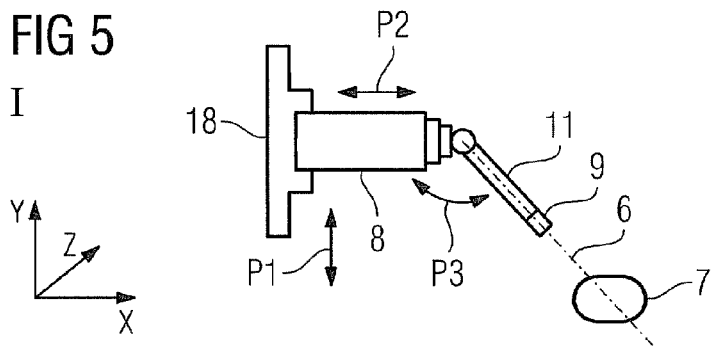
FIG. 5 shows in diagrammatic form an exemplary embodiment for the course of movement of a carrier arm.

FIG. 5 shows the carrier arm 8 of an exemplary embodiment in different system attitudes or positions. The carrier arm 8 is embodied as a telescopic arm. Via an intermediate piece 11 the x-ray source 9 is arranged in a rotatable manner on the carrier arm 8, in order to be able to direct the x-ray cone towards the object at all times. The viewing axis 6 runs from the x-ray source 9 to the object to be represented 7. The carrier arm 8 is represented in three different system attitudes or positions (I, II, III). The entire carrier arm 8 is movable in direction P1 or in the Y-direction via rails 18. The carrier arm is here extendable in the direction P2 and can thus change the position of its tip in the X-direction. A movement in the Z-direction too is for example possible by means of rail system (not shown here). This applies equally to the x-ray detector (not shown). During the movement from position 1 (I) to position 2 (II) the telescopic arm 8 is extended along a straight line and the x-ray source 9 brought from an oblique into a vertical attitude corresponding to the viewing axis 6. During the movement from position 2 (II) to position 3 (III) the x-ray source 9 is swiveled into an opposite oblique location according to the viewing axis 6. This has the result that the scan path of x-ray source 3 does not run in a linear manner. In order to traverse a preprogrammed straight-line scan path 1, this movement must be offset in the Y-direction by means of a movement of the carrier of the telescopic arm along the rail 18.

Figure 6:
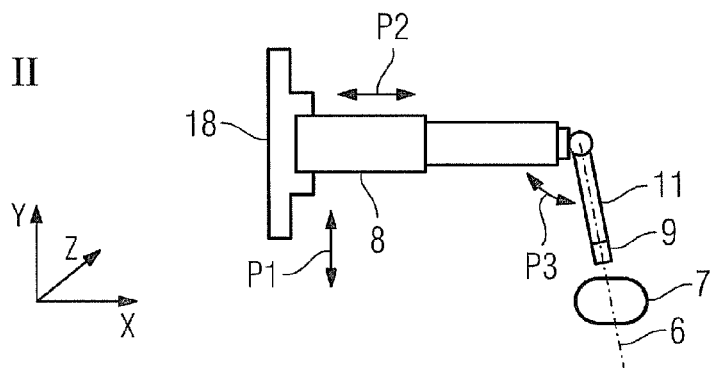
FIG. 6 shows in diagrammatic form the scan paths for the exemplary embodiment of FIG. 5.
Figure 6:
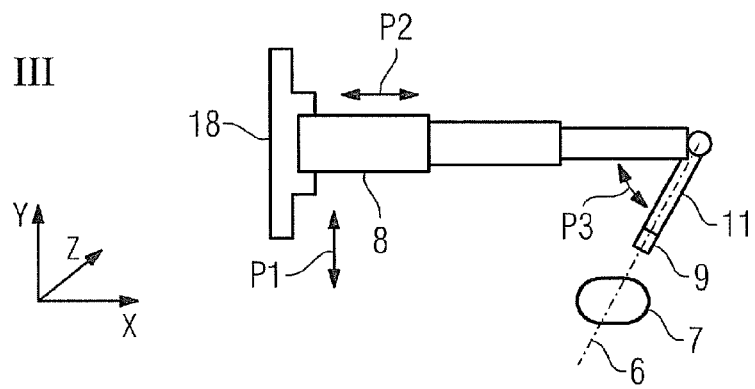
Figure 6:
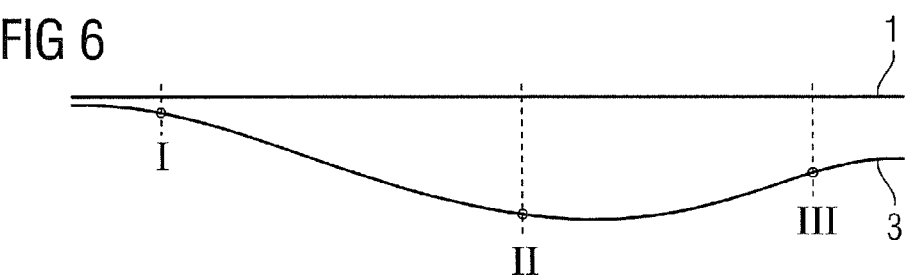

FIG. 6 shows the scan path of the x-ray detector for the exemplary embodiment according to FIG. 5. The original scan path 1 of the x-ray detector runs in a straight line. The modified scan path of the x-ray detector 3 runs in a curve. This corresponds to the actual movement of the x-ray source 9 itself in the case of a straight-line movement of the carrier arm 8 in direction P2, and without movement of the carrier of the telescopic arm 18 in direction P1 (Y-direction). The positions 1-3 (I, II, III) are marked on the scan paths.

Figure 7:
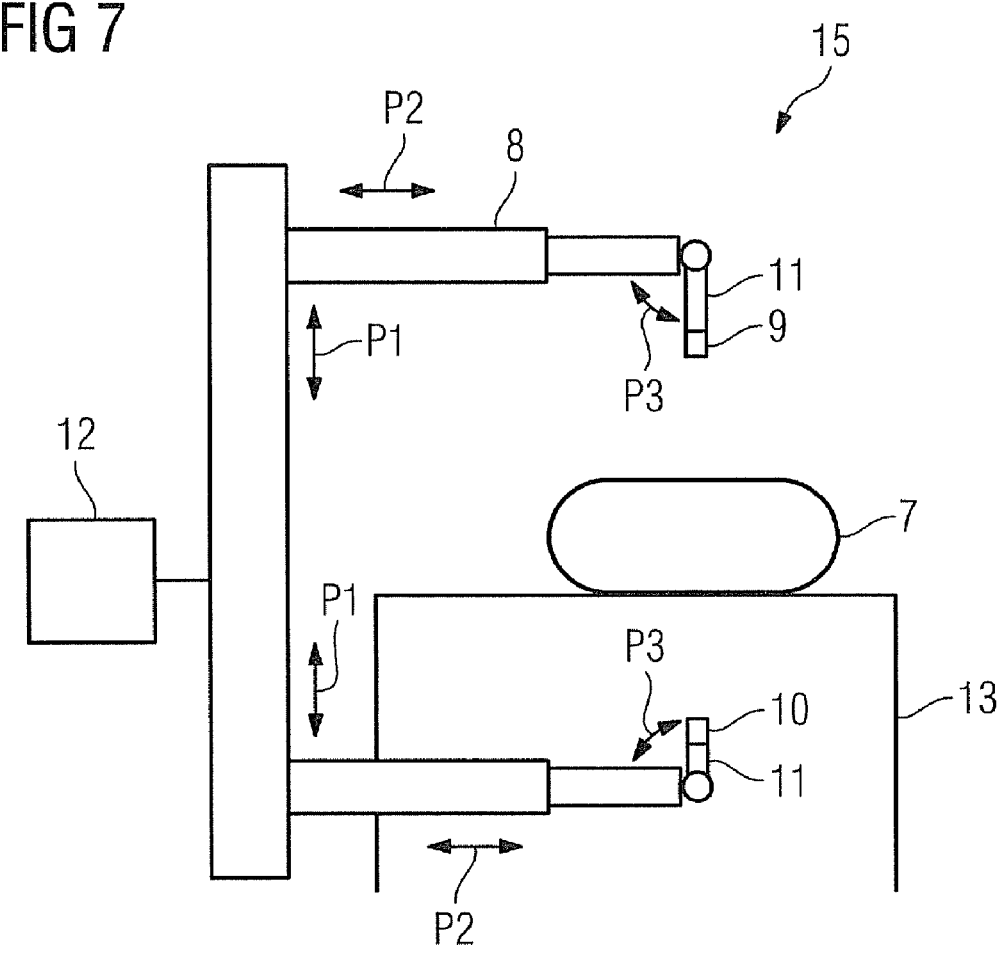
FIG. 7 shows in diagrammatic form an exemplary embodiment for an inventive x-ray system.

FIG. 7 shows in diagrammatic form the structure of an exemplary embodiment of the inventive x-ray system 15. The object 7 to be imaged is placed on a couch 13. The object 7 is as a rule a patient. Above the object 7 is located a carrier arm 8, on which the x-ray source 9 is arranged via an intermediate piece 11. Under the object 7 is located a further carrier arm 8, on which the x-ray detector is arranged via a further intermediate piece. An actuation and data processing unit 12 serves the imaging on the x-ray system 15.

The carrier arms 8 are here extendable in the X-direction or in direction P2. Via for example a rail system each carrier arm can be moved in the Y-direction or in direction P1. Not shown in this two-dimensional representation is the movement in the Z-direction, which can likewise be enabled by means of a rail system, but also by means of a swiveling to a horizontal plane. The intermediate piece 11 with the x-ray source 9 or detector 10 arranged thereupon can be swiveled opposite the carrier arm 8.

LIST OF REFERENCE CHARACTERS

Original scan path of the x-ray source
Original scan path of the x-ray detector
Modified scan path of the x-ray source
Modified scan path of the x-ray detector
5a Movement of the carrier arm tip on the x-ray source
5b Movement of the carrier arm tip on the x-ray detector
6a-g Viewing axis
7 Object
8 Carrier arm
9 x-ray source
10 x-ray detector
11 Intermediate piece
12 Actuation and data processing unit
13 Couch
15 x-ray system
18 Rail 21 Acquisition point of the x-ray source
22 Acquisition point of the x-ray detector
V Displacement
I Position 1
II Position 2
III Position 3
P1 Vertical movement
P2 Horizontal movement
P3 Rotational movement

The invention claimed is:

1. A method for generating a scan path for an x-ray source and/or an x-ray detector of an x-ray system, comprising:
   defining an original scan path of the x-ray source and/or of the x-ray detector by a series of original acquisition points of an object;
   identifying a viewing axis from the x-ray source to the object and/or to the detector for at least one of the original acquisition points on the scan path; and
   generating a modified scan path by displacing the at least one of the acquisition points partially along the viewing axis so that a same scanning movement of the x-ray system upon traversing the modified scan path is reproduced as traversing the original scan path.

2. The method as claimed in claim 1, wherein the x-ray source and/or the x-ray detector is moved on a carrier device having different degrees of freedom.

3. The method as claimed in claim 1, wherein the x-ray system requires fewer motors and/or motor movements for traversing the modified scan path than for traversing the original scan path.

4. The method as claimed in claim 1, wherein the viewing axis runs through a focal spot of the x-ray source and a defined point on the detector.

5. The method as claimed in claim 1, wherein motor movements necessary for traversing the original scan path and the modified scan path is programmed in the x-ray system.

6. The method as claimed in claim 1, wherein the modified scan path is calculated by an analytical method.

7. The method as claimed in claim 1, wherein the modified scan path is calculated by a numeric method.

8. The method as claimed in claim 1, wherein the original scan path comprises one or a multiplicity of straight lines.

9. The method as claimed in claim 1, wherein the modified scan path comprises a partially curved course.

10. The method as claimed in claim 1, wherein the x-ray source and/or of the x-ray detector traverses partially the original scan path when traversing in the modified scan path.

11. An x-ray system, comprising:
    an x-ray source;
    an x-ray detector; and
    a computer that:
       defines an original scan path of the x-ray source and/or of the x-ray detector by a series of original acquisition points of an object;
       identifies a viewing axis from the x-ray source to the object and/or to the detector for at least one of the original acquisition points on the scan path; and
       generates a modified scan path by displacing the at least one of the original acquisition points partially along the viewing axis so that a same scanning movement of the x-ray system upon traversing the modified scan path is reproduced as traversing the original scan path.

12. A non-transitory computer-readable medium encoded with a computer program for generating a scan path for an x-ray source and/or an x-ray detector of an x-ray system, wherein the computer program performs the following steps when executed on a computer:
    defining an original scan path of the x-ray source and/or of the x-ray detector by a series of original acquisition points of an object;
    identifying a viewing axis from the x-ray source to the object and/or to the detector for at least one of the original acquisition points on the scan path; and
    generating a modified scan path by displacing the at least one of the acquisition points partially along the viewing axis so that a same scanning movement of the x-ray system upon traversing the modified scan path is reproduced as traversing the original scan path.

* * * * *